United States Patent [19]

Shimada et al.

[11] Patent Number: 5,480,753
[45] Date of Patent: Jan. 2, 1996

[54] ELECTROPHOTOGRAPHIC PHOTOCONDUCTOR COMPRISING DIAMINE COMPOUND

[75] Inventors: Tomoyuki Shimada, Shizuoka; Masaomi Sasaki, Susono; Chiaki Tanaka, Shizuoka, all of Japan

[73] Assignee: Ricoh Company, Ltd., Tokyo, Japan

[21] Appl. No.: 277,024

[22] Filed: Jul. 19, 1994

Related U.S. Application Data

[63] Continuation-in-part of Ser. No. 202,238, Feb. 25, 1994, Pat. No. 5,420,332.

[30] Foreign Application Priority Data

| Feb. 26, 1993 | [JP] | Japan | 5-062773 |
| Jun. 15, 1993 | [JP] | Japan | 5-168515 |
| Jul. 19, 1993 | [JP] | Japan | 5-200061 |
| Aug. 9, 1993 | [JP] | Japan | 5-217030 |
| Sep. 2, 1993 | [JP] | Japan | 5-242070 |
| Dec. 7, 1993 | [JP] | Japan | 5-340078 |

[51] Int. Cl.$^6$ .................................................. G03G 5/047
[52] U.S. Cl. ....................................... 430/59; 430/83
[58] Field of Search ................................. 430/58, 59, 69, 430/66, 67, 83

[56] References Cited

U.S. PATENT DOCUMENTS

| 5,310,613 | 5/1994 | Pai et al. | 430/59 |
| 5,322,753 | 6/1994 | Tamura et al. | 430/59 |
| 5,356,743 | 10/1994 | Yanos et al. | 430/59 |

*Primary Examiner*—John Goodrow
*Attorney, Agent, or Firm*—Oblon, Spivak, McClelland, Maier & Neustadt

[57] ABSTRACT

An electrophotographic photoconductor is composed of an electroconductive support, and a photoconductive layer formed thereon which contains as a photoconductive material at least one diamine compound having carbonate groups of formula (I):

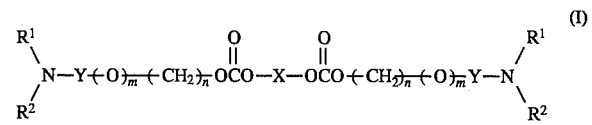

wherein $R^1$ and $R^2$ each is hydrogen, an alkyl group, or an aryl group; $R^1$ and $R^2$ may form a ring in combination of N bonded thereto; Y is an arylene group,

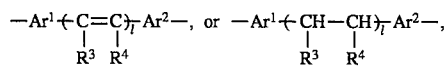

wherein $Ar^1$ and $Ar^2$ each is an arylene group, $R^3$ and $R^4$ each is hydrogen, an alkyl group, or an aryl group, and l is an integer of 1 or 2; and $R^1$ and Y may together form a ring, X is an alkylene group, a dialkylene ether group or an arylene group, —$Ar^3$-Z-$Ar^4$—, wherein $Ar^3$ and $Ar^4$ each is an arylene group; Z is an alkylene group, a dialkylene ether group or a cycloalkylidene group, oxygen, sulfur, a vinylene group, m is an integer of 0 or 1; and n is an integer of 0 to 6.

6 Claims, 2 Drawing Sheets

ELECTROPHOTOGRAPHIC PHOTOCONDUCTOR COMPRISING DIAMINE COMPOUND

This application is a continuation-in-part of application Ser. No. 08/202,238, filed Feb. 25, 1994, now U.S. Pat. No. 5,420,332.

BACKGROUND OF THE INVENTION

1. Field of the Invention

The present invention relates to an electrophotographic photoconductor comprising an electroconductive support end a photoconductive layer formed thereon, which comprises a diamine compound as a photoconductive material.

2. Discussion of Background

Conventionally, inorganic materials such as selenium, cadmium sulfide end zinc oxide are used as photoconductive materials of an electrophotographic photoconductor in an electrophotographic process.

The electrophotographic process is one of the image formation processes, through which the surface of the photoconductor is charged uniformly in the dark to a predetermined polarity, for instance, by corona charging. The uniformly charged photoconductor is exposed to a light image to selectively dissipate the electric charges of the exposed areas, so that a latent electrostatic image is formed on the photoconductor. The thus formed latent electrostatic image is developed into a visible toner image by a toner or developer comprising a coloring agent such as a dye or pigment, and a binder agent such as a polymeric material.

Fundamental characteristics required for the photoconductor in such an electrophotographic process are: (1) chargeability to an appropriate potential in the dark, (2) minimum dissipation of electrical charges in the dark, and (3) rapid dissipation of electrical charges when exposed to light.

However, while the above-mentioned inorganic materials have many advantages, they have several shortcomings from the viewpoint of practical use.

For instance, a selenium photoconductor, which is widely used as present, satisfies the above-mentioned requirements (1) to (3) completely, but it has the shortcomings that the manufacturing conditions are difficult and, accordingly, its production cost is high. In addition, it is difficult to work it into the form of a belt due to its poor flexibility, and it is so vulnerable to heat and mechanical shocks that it must be handled with the utmost care.

A cadmium sulfide photoconductor and a zinc oxide photoconductor can be easily obtained by dispersing cadmium sulfide particles and zinc oxide particles respectively in a binder resin, and coating the thus prepared coating liquid on a support. However, they are poor in mechanical properties, such as surface smoothness, hardness, tensile strength and wear resistance. Therefore, they cannot be used repeated as they are.

To solve the problems of the inorganic materials, various electrophotographic photoconductors employing organic materials have recently been proposed and some are already used practically. For example, there are known a photoconductor comprising poly-N-vinylcarbazole and 2,4,7-trinitrofluorene-9-on, as disclosed in U.S. Pat. No. 3,484,237; a photoconductor prepared by sensitizing poly-N-vinylcarbazole with a pigment of pyrylium salt, as disclosed in Japanese Patent Publication 48-25658; a photoconductor comprising as the main component an organic pigment as disclosed in Japanese Laid-Open Patent Application 47-37543; a photoconductor comprising as the main component a eutectic crystal complex of a dye and a resin, as disclosed in Japanese Laid-Open Patent Application 47-10735; a photoconductor prepared by sensitizing a triphenylamine compound with a sensitizer pigment, as disclosed in U.S. Pat. No. 3,180,730; a photoconductor comprising an amine derivative as a charge transporting material, as disclosed in Japanese Laid-Open Patent Application 57-195254; a photoconductor comprising poly-N-vinylcarbazole and an amine derivative as charge transporting materials, as disclosed in Japanese Laid-Open Patent Application 58-1155; and a photoconductor comprising as a photoconductive material a polyfunctional tertiary amine compound, in particular, a benzidine compound, as disclosed in U.S. Pat. No. 3,265,496, Japanese Patent Publication 39-11546 and Japanese Laid-Open Patent Application 53-27033.

These electrophotographic photoconductors have their own excellent characteristics and considered to be valuable for use in practice. With various requirements of the electrophotographic photoconductor in the electrophotographic process taken into consideration, however, the above-mentioned conventional electrophotographic photoconductors cannot always meet all of the above-mentioned requirements.

Electrophotographic photoconductors which comprise carbonate-group-containing compounds as the photoconductive materials are disclosed in U.S. Pat. Nos. 4,801,517, 4,806,443 and 4,806,444, and Japanese Laid-Open Patent Applications Nos. 3-221522 and 4-11627. Each of the carbonate-group-containing compounds for use in the photoconductors is a polymeric compound, so that it is difficult to purify the carbonate-group-containing compound by column chromatography, recrystallization, distillation or sublimation in order to obtain such a high purity as required for the photoconductive material. Therefore, impurities cannot completely be removed from the above-mentioned photoconductors, so that not all the requirements for the photoconductor can be satisfied.

There is widely used an electrophotographic photoconductor of which photoconductive layer is prepared in such a manner that a low-molecular photoconductive material is dissolved or dispersed in a binder resin solution to form a resin composition and the photoconductive layer is formed by casting the above prepared resin composition. However, when the photoconductive layer is formed by using a mixture of the low-molecular photoconductive material and the binder resin, as mentioned, the resin solution of the photoconductive material easily tends to cause gelation to become white opaque, and induces phase separation depending on the kind of binder resin employed. As a result, a uniform photoconductive layer cannot be obtained, which has an adverse effect on the electrostatic properties and the durability of the photoconductor.

Furthermore, as described in Japanese Laid-Open Patent Application 3-221522, there are the problems of the gelation of a photoconductive layer coating liquid, and partial crystallization and cracks of the obtained photoconductive layer when a single high-molecular photoconductive material is used to prepare a coating liquid for the photoconductive layer. According to the description in the aforementioned application, it is required that the copolymerization ratio of the high-molecular photoconductive material be controlled and the viscosity of the coating liquid for the photoconductive layer be adjusted to solve the above-mentioned problems.

SUMMARY OF THE INVENTION

It is therefore an object of the present invention to provide an electrophotographic photo-conductor comprising a photoconductive material, free from the conventional shortcomings, which can completely satisfy all the requirements in the electrophotographic process, including high durability, and can be easily be manufactured at relatively low cost.

The above-mentioned object of the present invention can be achieved by an electrophotographic photoconductor comprising an electroconductive support and a photoconductive layer formed thereon comprising as a photoconductive material at least one diamine compound having carbonate groups of formula (I):

$$\begin{array}{c}R^1\\ \diagdown\\ R^2 \diagup\end{array} N-Y(O)_{\overline{m}}(CH_2)_{\overline{n}} OCO-X-OCO(CH_2)_{\overline{n}}(O)_{\overline{m}} Y-N \begin{array}{c}\diagup R^1\\ \diagdown R^2\end{array} \quad (I)$$

wherein $R^1$ and $R^2$ each is a hydrogen atom, an alkyl group which may have a substituent, an aryl group which may have a substituent; $R^1$ and $R^2$ may form a ring in combination of N bonded thereto; Y is an arylene group which may have a substituent, $$-Ar^1(C=C)_{\overline{l}} Ar^2-, \text{ or } -Ar^1(CH-CH)_{\overline{l}} Ar^2-,$$
$$\quad\quad R^3\ R^4 \quad\quad\quad\quad\quad R^3\ R^4$$

in which $Ar^1$ and $Ar^2$ each is an arylene group which may have a substituent, $R^3$ and $R^4$ each is a hydrogen atom, an alkyl group which may have a substituent, or an aryl group which may have a substituent, and l is an integer of 1 or 2; and $R^1$ and Y may together form a ring, X is an alkylene group which may have a substituent, a dialkylene ether group, or an arylene group which may have a substituent, $$-Ar^3-Z-Ar^4-,$$

in which $Ar^3$ and $Ar^4$ each is an arylene group which may have a substituent; Z is an alkylene group which may have a substituent, a dialkylene ether group or a cycloalkylidene group which may have a substituent, an oxygen atom, a sulfur atom, or a vinylene group, m is an integer of 0 or 1; and n is an integer of 0 to 6.

BRIEF DESCRIPTION OF THE DRAWINGS

A more complete appreciation Of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
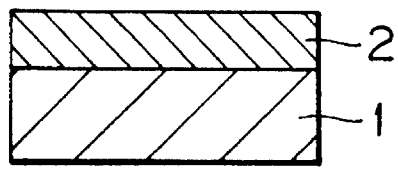
FIG. 1 is a schematic cross-sectional view of a first example of an electrophotographic photoconductor according to the present invention.

An electrophotographic photoconductor according to the present invention comprises an electroconductive support and a photoconductive layer formed thereon comprising as a photoconductive material at least one diamine compound having carbonate groups of formula (I):

$$\begin{array}{c}R^1\\ \diagdown\\ R^2 \diagup\end{array} N-Y(O)_{\overline{m}}(CH_2)_{\overline{n}} OCO-X-OCO(CH_2)_{\overline{n}}(O)_{\overline{m}} Y-N \begin{array}{c}\diagup R^1\\ \diagdown R^2\end{array} \quad (I)$$

wherein $R^1$ and $R^2$ each is a hydrogen atom, an alkyl group which may have a substituent, an aryl group which may have a substituent; $R^1$ and $R^2$ may form a ring in combination of N bonded thereto; Y is an arylene group which may have a substituent, $$-Ar^1(C=C)_{\overline{l}} Ar^2-, \text{ or } -Ar^1(CH-CH)_{\overline{l}} Ar^2-,$$
$$\quad\quad R^3\ R^4 \quad\quad\quad\quad\quad R^3\ R^4$$

in which $Ar^1$ and $Ar^2$ each is in arylene group which may have a substituent, $R^3$ and $R^4$ each is a hydrogen atom, an alkyl group which may have a substituent, or an aryl group which may have a substituent, and l is an integer of 1 or 2; and $R^1$ and Y may together form a ring, X is an alkylene group which may have a substituent, a dialkylene ether group, or an arylene group which may have a substituent, $$-Ar^3-Z-Ar^4-,$$

in which $Ar^3$ and $Ar^4$ each is an arylene group which may have a substituent; Z is an alkylene group which may have a substituent, a dialkylene ether group, or a cycloalkylidene group which may have a substituent, an oxygen atom, a sulfur atom, or a vinylene group, m is an integer of 0 or 1; and n is an integer of 0 to 6.

specific examples of $R^1$ to $R^4$, $Ar^1$ to $Ar^4$, X, Y and Z, and the substituents thereof in formula (I) are as follows:

(1) Hydrogen atom.

(2) Halogen atom such as fluorine, chloride, bromine and iodine.

(3) Cyano group.

(4) Nitro group.

(5) Hydroxy group.

(6) Alkyl group represented by (—$R^5$), in particular a straight-chain or branched-chain alkyl group having 1 to 12 carbon atoms, more preferably 1 to 9 carbon atoms, further more preferably 1 to 4 carbon atoms. This alkyl group may have a substituent such as a fluorine atom, a hydroxyl group, a cyano group, an alkoxyl group having 1 to 4 carbon atoms, a phenyl group which may have a substituent such as an alkyl group having 1 to 4 carbon atoms or an alkoxyl group having 1 to 4 carbon atoms, and a halogen.

Specific examples of the above alkyl group include methyl group, ethyl group, n-propyl group, i-propyl group, tert-butyl group, sec-butyl group, n-butyl group, i-butyl group, trifluoromethyl group, 2-phenylethyl group, 2-hydroxyethyl group, 2-cyanoethyl group, 2-ethoxyethyl group, 2-methoxyethyl group, benzyl group, 4-chlorobenzyl group, 4-methylbenzyl group, 4-methoxybenzyl group and 4-phenylbenzyl group.

(7) Alkoxyl group represented by —OR$^5$, in which R$^5$ is the same alkyl group as defined in (6).

Specific examples of the above alkoxyl group include methoxy group, ethoxy group, n-propoxy group, i-propoxy group, tert-butoxy group, n-butoxy group, sec-butoxy group, i-butoxy group, 2-hydroxyethoxy group, 2-cyanoethoxy group, benzyloxy group, 4-methylbenzyloxy group and trifluoromethoxy group.

(8) Alkylthio group represented by —SR$^5$, in which R$^5$ represents the same alkyl group as defined in (6).

Specific examples of the above alkylthio group include methylthio group, ethylthio group, benzylthio group and hydroxyethylthio group.

(9) Alkylene group represented by —R$^6$—, which is a bivalent group derived from the alkyl group defined in (6).

Specific examples of the above alkylene group include methylene group, ethylene group, 1,3-propylene group, 1,4-butylene group, 2-methyl-1,3-propylene group, difluoromethylene group, hydroxyethylene group, cyanoethylene group, methoxyethylene group, phenylmethylene group, 4-methylphenylmethylene group, propylene group, 2,2-butylene group and diphenylmethylene group.

(10) Dialkylene ether group represented by —R$^7$-O-R$^8$—; in which R$^7$ and R$^8$ represent the same alkylene group as defined in (9).

Specific examples of the above dialkylene ether group include dimethylene ether group, diethylene ether group, and methylene ethylene ether group.

(11) Cycloalkylidene group of the following formula:

$$\underset{CH_2 \quad K}{\overset{\diagdown \quad \diagup}{\underset{}{\overset{C}{\diagup\diagdown}}}}$$

in which K is an integer of 4 to 10.

Specific examples of the above cycloalkylidene group include 1,1-cyclopentylidene group, 1,1-cyclohexylidene group, and 1,1-cyclooctylidene group.

(12) Aryl group represented by —Ar$^5$, such as a cyclic hydrocarbon aromatic group and a heterocyclic aromatic group.

Specific examples of the above cyclic hydrocarbon aromatic group include phenyl group, biphenyl group, terphenyl group, pentalenyl group, indenyl group, naphthyl group, azulenyl group, heptalenyl group, biphenylenyl group, as-indacenyl group, fluorenyl group, s-indacenyl group, acenaphthylenyl group, pleiadenyl group, acenaphthenyl group, phenalenyl group, phenanthryl group, anthryl group, fluoranthenyl group, acephenanthrylenyl group, aceanthrylenyl group, triphenylenyl group, pyrenyl group, chrysenyl group and naphthacenyl group.

Specific examples of the above heterocyclic aromatic group include pyridyl group, pyrimidyl group, pyrazinyl group, triazinyl group, furyl group, pyrrolyl group, thienyl group, quinolyl group, coumarinyl group, benzofuranyl group, benzimidazolyl group, benzoxazolyl group, dibenzofuranyl group, benzothienyl group, dibenzothionyl group, indolyl group, carbazolyl group, pyrazolyl group, imidazolyl group, oxazolyl group, isooxazolyl group, thiazolyl group, indazolyl group, benzothiazolyl group, pyridazinyl group, cinnolinyl group, quinazolinyl group, quinoxalyl group, phthalazinyl group, phthalazinedionyl group, chromonyl group, naphtholactonyl group, quinolonyl group, o-sulfobenzoic acid imidyl group, maleic acid imidyl group, naphthalidinyl group, benzimidazolonyl group, benzoxazolonyl group, benzothiazolonyl group, benzothiazothionyl group, quinazolonyl group, quinoxalonyl group, phthalazonyl group, dioxopyrimidinyl group, pyridonyl group, isoquinolonyl group, isoquinolyl group, isothiazolyl group, benzisooxazolyl group, benzisothiazolyl group, indazolonyl group, acridinyl group, acridonyl group, quinazolinedionyl group, quinoxalinedionyl group, benzoxazinedionyl group, benzoxazinyl group, and naphthalimidyl group. These aryl groups may have a substituent as mentioned in (2) to (8).

(13) Aryloxy group represented by —OAr$^5$, in which Ar$^5$ represents the same aryl group as defined in (12).

Specific examples of the above aryloxy group include phenoxy group, 4-methylphenoxy group and naphthoxy group.

(14) Arylthio group represented by —SAr$^5$, in which Ar$^5$ represents the same aryl group as defined in (12).

Specific examples of the above arylthio group include phenylthio group and naphthylthio group.

(15) Arylene group represented by —Ar$^6$—; in which —Ar$^5$— is a bivalent group derived from the aryl group defined in (12).

Specific examples of the above arylene group include phenylene group, biphenylene group, pyrenylene group, and N-ethylcarbazolylene.

(16) Amino group represented by —N(R$^9$)(R$^{10}$), in which R$^9$ and R$^{10}$ each is a hydrogen atom, the same alkyl group as defined in (6), or the same aryl group as defined in (12), and R$^9$ and R$^{10}$ may together form a ring.

Specific examples of the above amino group include amino group, diethylamino group, N-methyl-N-phenylamino group, N,N-diphenylamino group, N,N-di(p-tolyl)amino group, dibenzylamino group, piperidino group, morpholino group and julolidino group.

(17) Vinyl group of any of the following formulae:

$$[(CH=CH)_{\overline{j}}CH=\underset{R_{12}}{\overset{|}{C}}-R^{11}], \text{ or } [(CH=CH)_{\overline{j}}CH=\underset{R_{14}-W}{\overset{|}{C}}-R^{13}],$$

in which R$^{11}$ and R$^{12}$ each represents the same substituent as defined in (1) to (5), and (12) to (14), R$^{13}$ and R$^{14}$ represent the same substituent as defined in (9), (10) and (15); j is an integer of 0 or 1; and W is an oxygen atom, a sulfur atom, and a vinylene group or an alkylene group.

Specific examples of the above vinyl group include styryl group, 4-methylstyryl group, β-methylstyryl group, 4-chlorostyryl group, β-phenylstyryl group, β-(4-methylphenyl)styryl group, and 4-phenyl-1,3-butadienyl group.

The diamine compound of formula (I) for use in the present invention can be prepared by allowing a hydroxy compound of formula (II):

$$\underset{R^2}{\overset{R^1}{\diagdown}}N-Y(O)_{\overline{m}}(CH_2)_{\overline{n}}OH \qquad (II)$$

wherein R$^1$, R$^2$, Y, m and n are respectively the same as those defined in formula (I), to react with a bis(chloroformate) compound of formula (III), wherein X is the same as defined in formula (I).

$$ClCO-X-OCCl \quad (III)$$

(with two C=O groups)

Specific examples of the above hydroxy compound of formula (II) and the bis(chloroformate) compound of formula (III) are shown in the following TABLES 1, 2 and 3:

TABLE 1

$$HO\text{-}(CH_2)_n\text{-}Y\text{-}N\begin{matrix}R^1\\R^2\end{matrix} \quad [m=0]$$

| Hydroxy Comp. No. | Y | R¹ | R² | n |
|---|---|---|---|---|
| 1 | –C₆H₄– (para) | –C₆H₅ | –C₆H₅ | 0 |
| 2 | –C₆H₄– (para) | –C₆H₄–CH₃ | –C₆H₄–CH₃ | 0 |
| 3 | –C₆H₄–C₆H₄– | –C₆H₄–CH₃ | –C₆H₄–CH₃ | 0 |
| 4 | –C₆H₄– | –C₆H₄–CH₃ | –C₆H₄–CH₃ | 0 |
| 5 | –C₆H₄–CH=CH–C₆H₄– | –C₆H₄–CH₃ | –C₆H₄–CH₃ | 0 |
| 6 | –C₆H₄–CH=CH–C₆H₄– | –C₆H₅ | –C₆H₅ | 0 |
| 7 | –C₆H₄–CH=CH–C₆H₄– (meta) | –C₆H₅ | –C₆H₅ | 0 |
| 8 | –C₆H₄–CH=CH–C₆H₄– (meta) | –C₆H₄–CH₃ | –C₆H₄–CH₃ | 0 |
| 9 | –C₆H₄– | –C₆H₄–C₆H₄–CH₃ | –C₆H₄–CH₃ | 0 |
| 10 | –C₆H₄– | –(pyrene) | –C₆H₄–CH₃ | 0 |

TABLE 1-continued
$$HO\text{-}(CH_2)_n\text{-}Y\text{-}N\begin{matrix}R^1\\R^2\end{matrix} \quad [m=0]$$
| Hydroxy Comp. No. | Y | R¹ | R² | n |
|---|---|---|---|---|
| 11 | 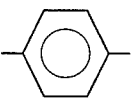 | 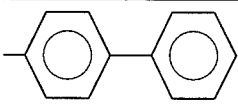 | 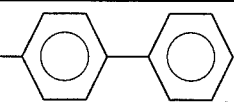 | 0 |
| 12 | 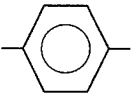 | 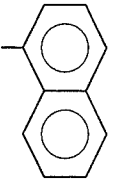 | 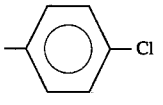 | 0 |
| 13 | 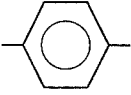 | —CH₃ | —CH₃ | 0 |
| 14 |  | 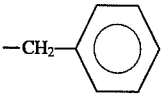 | 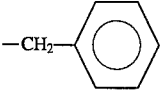 | 0 |
| 15 | 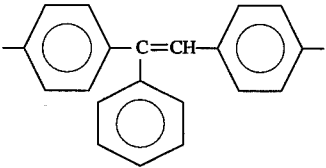 | 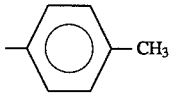 | 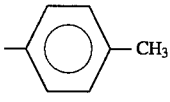 | 0 |
| 16 | 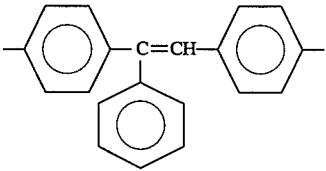 | 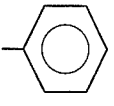 | 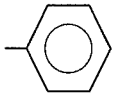 | 0 |
| 17 | 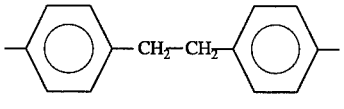 | 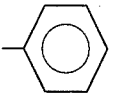 | 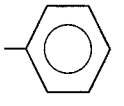 | 0 |
| 18 | 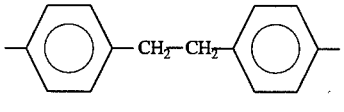 | 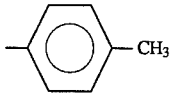 | 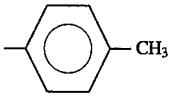 | 0 |
| 19 | 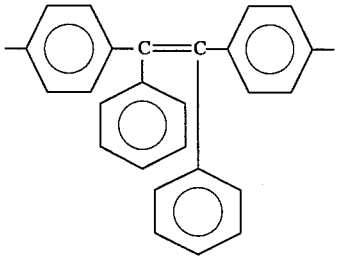 | —C₂H₅ | 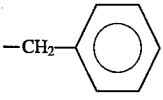 | 0 |

TABLE 1-continued $$HO\text{---}(CH_2)_n\text{---}Y\text{---}N\begin{matrix}R^1\\R^2\end{matrix} \quad [m=0]$$

| Hydroxy Comp. No. | Y | R¹ | R² | n |
|---|---|---|---|---|
| 20 | –C₆H₄– | 4-(2,2-diphenylvinyl)phenyl | phenyl | 0 |
| 21 | –C₆H₄– | phenyl | phenyl | 1 |
| 22 | –C₆H₄– | 4-methylphenyl | 4-methylphenyl | 1 |
| 23 | –C₆H₄– | 4-methoxyphenyl | 4-methoxyphenyl | 1 |
| 24 | –C₆H₄– | 4'-methylbiphenyl-4-yl | 4-methylphenyl | 1 |
| 25 | –C₆H₄– | 4-(2-(dibenzo[a,d]cyclohepten-5-ylidene)methyl)phenyl | 4-methylphenyl | 1 |
| 26 | –C₆H₄– | pyrenyl | 4'-methylbiphenyl-4-yl | 1 |
| 27 | –C₆H₄– | pyrenyl | phenyl | 1 |

TABLE 1-continued
$$HO-(CH_2)_n-Y-N\begin{matrix}R^1\\R^2\end{matrix} \quad [m=0]$$
| Hydroxy Comp. No. | Y | R¹ | R² | n |
|---|---|---|---|---|
| 28 | 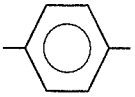 | 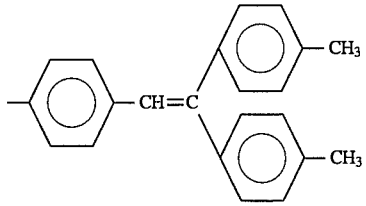 | 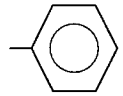 | 1 |
| 29 |  | 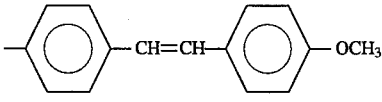 | 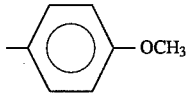 | 1 |
| 30 |  |  | 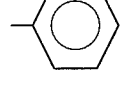 | 2 |
| 31 |  | 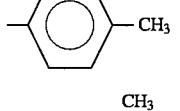 | 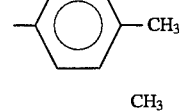 | 2 |
| 32 |  | 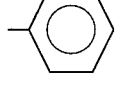 | 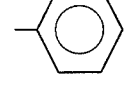 | 2 |
| 33 | 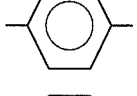 | 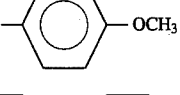 | 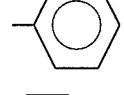 | 2 |
| 34 |  |  |  | 2 |
| 35 |  | 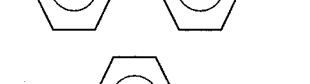 |  | 2 |
| 36 | 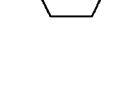 | 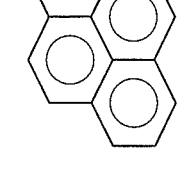 | 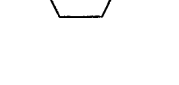 | 2 |
| 37 | 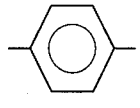 | 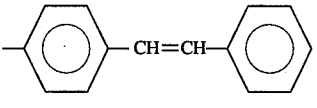 | 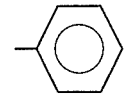 | 2 |

TABLE 1-continued $$HO\text{-}(CH_2)_{\overline{n}}\text{-}Y\text{-}N\begin{matrix}R^1\\R^2\end{matrix} \quad [m = 0]$$

| Hydroxy Comp. No. | Y | R¹ | R² | n |
|---|---|---|---|---|
| 38 | —C₆H₄— | —C₆H₄—(CH=CH)₂—C₆H₅ | —C₆H₄—CH₃ | 2 |
| 39 | —C₆H₄—C₆H₄— | —C₆H₄—CH₃ | —C₆H₄—CH₃ | 2 |
| 40 | —C₆H₄—C₆H₄— | —C₆H₅ | —C₆H₅ | 2 |
| 41 | —C₆H₄—C₆H₄— | —C₆H₄—C₆H₄—CH₃ | —C₆H₄—CH₃ | 2 |
| 42 | —C₆H₄—O—C₆H₄— | —C₆H₄—C₂H₅ | —C₆H₄—C₂H₅ | 2 |
| 43 | naphthyl | —C₆H₄—CH₃ (ortho) | —C₆H₄—CH₃ (ortho) | 2 |
| 44 | —C₆H₄—CH=CH—C₆H₄— | —C₆H₄—CH₃ | —C₆H₄—CH₃ | 2 |
| 45 | —C₆H₄—(CH=CH)₂—C₆H₄— | —C₆H₅ | —C₆H₅ | 2 |
| 46 | thienyl (2,5-) | thienyl—CH₃ | thienyl—CH₃ | 2 |
| 47 | —C₆H₄— | —C₆H₄—O—C₆H₅ | —C₆H₄—O—C₆H₅ | 2 |

TABLE 1-continued
$$HO-(CH_2)_n-Y-N\begin{matrix}R^1\\R^2\end{matrix} \quad [m=0]$$
| Hydroxy Comp. No. | Y | R¹ | R² | n |
|---|---|---|---|---|
| 48 | 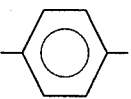 | 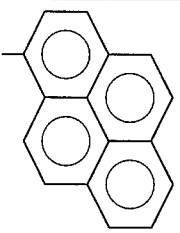 | 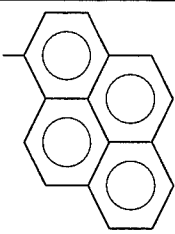 | 2 |
| 49 | 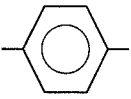 | 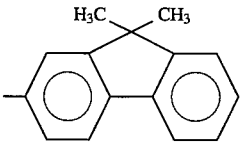 | 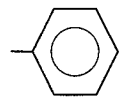 | 2 |
| 50 | 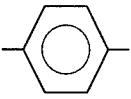 | 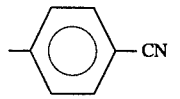 | 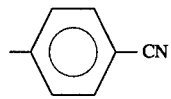 | 2 |
| 51 |  | H | 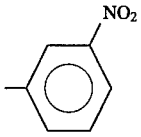 | 2 |
| 52 | 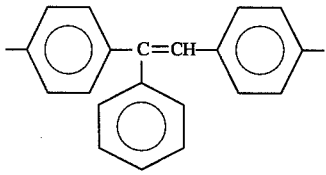 | 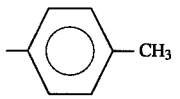 | 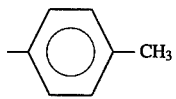 | 2 |
| 53 | 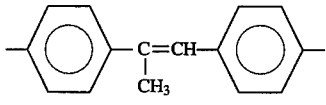 | 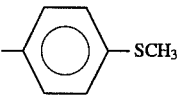 | 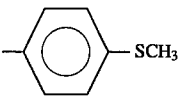 | 2 |
| 54 | 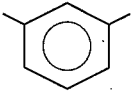 | 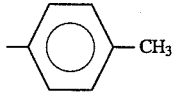 | 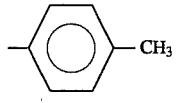 | 2 |
| 55 | 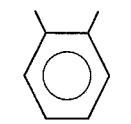 | 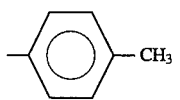 | 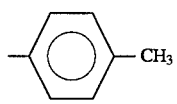 | 2 |

TABLE 1-continued
$$HO(CH_2)_n\text{-}Y\text{-}N\begin{matrix}R^1\\R^2\end{matrix} \quad [m=0]$$
| Hydroxy Comp. No. | Y | R¹ | R² | n |
|---|---|---|---|---|
| 56 |  | 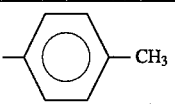 | 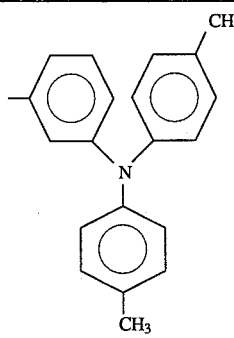 | 2 |
| 57 | | 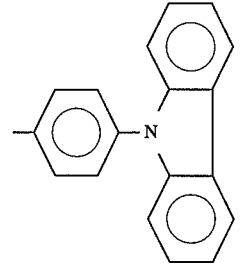 | | 0 |
| 58 | | 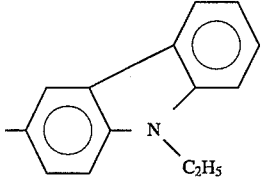 | | 1 |
| 59 | | 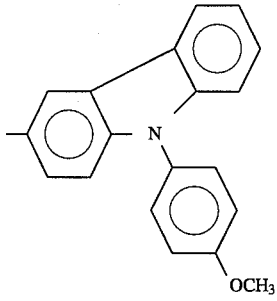 | | 1 |
| 60 | | 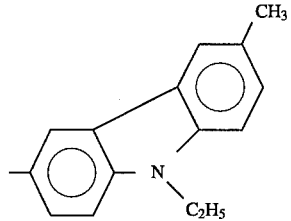 | | 1 |

TABLE 2
$$HO-(CH_2)_n-O-Y-N\begin{matrix}R^1\\R^2\end{matrix} \quad [m=1]$$
| Hydroxy Comp. No. | Y | R¹ | R² | n |
|---|---|---|---|---|
| 61 |  | $C_2H_5$ | $C_2H_5$ | 3 |
| 62 |  |  | 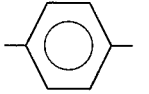 | 3 |
| 63 |  | 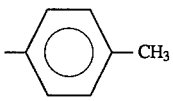—CH₃ | 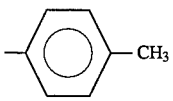—CH₃ | 3 |
| 64 | 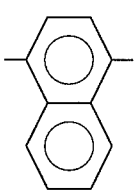 | 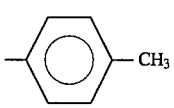—CH₃ | 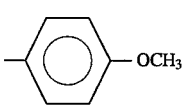—OCH₃ | 4 |
| 65 | 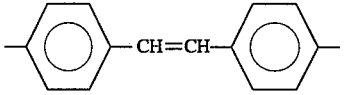—CH=CH—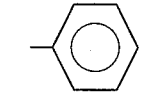 | 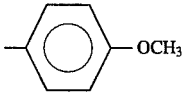 | 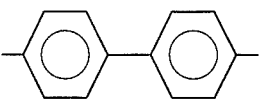—OCH₃ | 4 |
| 66 | 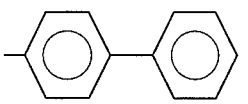 | 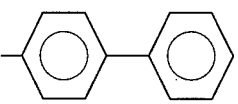 | 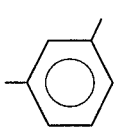 | 5 |
| 67 | 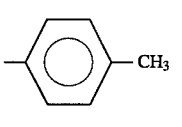 | 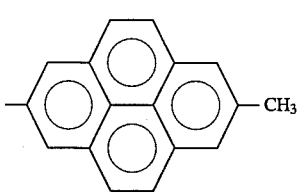—CH₃ | 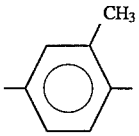—CH₃ | 5 |
| 68 | 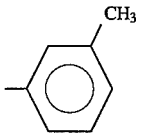 | 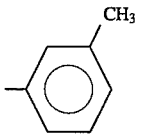 | 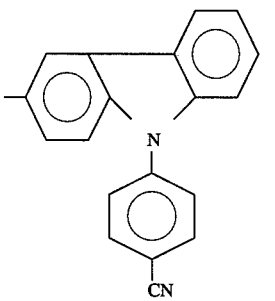 | 6 |
| 69 |  |  |  | 3 |

TABLE 3

$$\underset{\text{ClCO—X—OCCl}}{\overset{\text{O}\quad\quad\text{O}}{\|\quad\quad\|}}$$

| Bis (chloroformate Comp. No. | X |
|---|---|
| 1 | *p*-phenylene |
| 2 | 2,4-tolylene (methylphenylene) |
| 3 | 3-methyl-1,2-phenylene |
| 4 | 4,4'-biphenylene |
| 5 | 2,7-fluorenylene |
| 6 | pyrenylene |
| 7 | —CH₂CH₂CH₂CH₂— |
| 8 | —CH₂CH₂OCH₂CH₂— |
| 9 | —C₆H₄—CH₂—C₆H₄— |
| 10 | —C₆H₄—CH₂CH₂—C₆H₄— |
| 11 | —C₆H₄—C(CH₃)₂—C₆H₄— |
| 12 | —C₆H₄—C(CH₃)(C₂H₅)—C₆H₄— |
| 13 | —C₆H₄—C(C₂H₅)₂—C₆H₄— |
| 14 | —C₆H₄—C(CF₃)₂—C₆H₄— |
| 15 | —C₆H₄—C(CH₃)(C₆H₅)—C₆H₄— |
| 16 | —C₆H₄—C(C₆H₅)₂—C₆H₄— |
| 17 | —(3-CH₃-C₆H₃)—C(CH₃)₂—(3-CH₃-C₆H₃)— |
| 18 | —(3,5-(CH₃)₂-C₆H₂)—C(CH₃)₂—(3,5-(CH₃)₂-C₆H₂)— |
| 19 | —(3-C₆H₅-C₆H₃)—C(CH₃)₂—(3-C₆H₅-C₆H₃)— |
| 20 | —(3-Cl-C₆H₃)—C(CH₃)₂—(3-CH₃-C₆H₃)— |
| 21 | —C₆H₄—(1,1-cyclohexylidene)—C₆H₄— |

TABLE 3-continued $$\underset{ClCO-X-OCCl}{\overset{O\qquad O}{\overset{\|\qquad\|}{}}}$$

Bis (chloroformate Comp. No. | X
---|---
22 | (biphenyl-cyclohexyl(CH₃)-C(CH₃)₂-phenyl group)
23 | (biphenyl-fluorene-phenyl group)
24 | (biphenyl-phenyl-C(CH₃)(C(=O)O)- group)
25 | —⟨phenyl⟩—CH₂CH₂O—CH₂CH₂—⟨phenyl⟩—
26 | (fluorenone group)
27 | —⟨phenyl⟩—O—⟨phenyl⟩—
28 | —⟨phenyl⟩—S—⟨phenyl⟩—
29 | (phenyl-phenyl with pendant phenyl group)
30 | —⟨phenyl⟩—CH=CH—⟨phenyl⟩—

In the photoconductors according to the present invention, at least one diamine compound having carbonate groups of the formula (I) is contained in the photoconductive layers 2, 2a, 2b, 2c and 2d. The diamine compound can be employed in different ways, for example, as shown in FIGS. 1 through 5.

In the photoconductor as shown in FIG. 1, a photoconductive layer 2 is formed on an electroconductive support 1, which photoconductive layer 2 comprises at least one diamine compound of formula (I), a sensitizing dye and a binder agent (binder resin). In this photoconductor, the diamine compound works as a photoconductive material, through which charge carriers which are necessary for the light decay of the photoconductor are generated and transported. However, the diamine compound itself scarcely absorbs light in the visible light range, and therefore, it is necessary to add a sensitizing dye which absorbs light in the visible light range in order to form latent electrostatic images by use of visible light.

Figure 2:
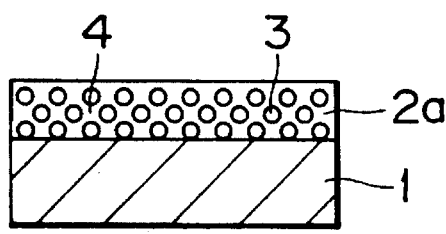
FIG. 2 is a schematic cross-sectional view of a second example of an electrophotographic photoconductor according to the present invention.

Referring to FIG. 2, there is shown an enlarged schematic cross-sectional view of another embodiment of an electrophotographic photoconductor according to the present invention. In the figure, reference numeral 1 indicates an electroconductive support. On the electroconductive support 1, there is formed a photoconductive layer 2a comprising a charge generating material 3 dispersed in a charge transporting medium 4 comprising at least one diamine compound of formula (I) and a binder agent. In this embodiment, the diamine compound and the binder agent (or a mixture of the binder agent and a plasticizer) in combination constitute the charge transporting medium 4. The charge generating material 3, which is, for example, an inorganic or organic pigment, generates charge carriers. The charge transporting medium 4 accepts the charge carriers generated by the charge generating material 3 and transports those charge carriers.

In this electrophotographic photoconductor, it is basically necessary that the light-absorption wavelength regions of the charge generating material 3 and the diamine compound not overlap in the visible light range. This is because, in order that the charge generating material 3 produce charge carriers efficiently, it is necessary that light pass through the charge transporting medium 4 and reach the surface of the charge generating material 3. Since the diamine compound of formula (I) does not substantially absorb light in the visible range, it can work effectively as a charge transporting material in combination with the charge generating material 3 which absorbs the light in the visible region and generates charge carriers.

Figure 3:
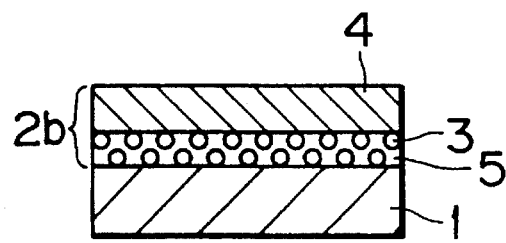
FIG. 3 is a schematic cross-sectional view of a third example of an electrophotographic photoconductor according to the present invention.

Referring to FIG. 3, there is shown an enlarged schematic cross-sectional view of a further embodiment of an electrophotographic photoconductor according to the present invention. In the figure, there is formed on an electroconductive support 1 a two-layered photoconductive layer 2b comprising a charge generation layer 5 containing the charge generating material 3, and a charge transport layer 4 containing at least one diamine compound of the previously described formula (I).

In this photoconductor, light which has passed through the charge transport layer 4 reaches the charge generation layer 5, and charge carriers are generated within the charge generation layer 5. The charge carriers which are necessary for the light decay for latent electrostatic image formation are generated by the charge generating material 3, and the charge carriers are accepted and transported by the charge transport layer 4. In the charge transport layer 4, the diamine compound mainly works for transporting charge carriers. The generation and transportation of the charge carriers are performed by the same mechanism as that in the photoconductor shown in FIG. 2.

Figure 4:
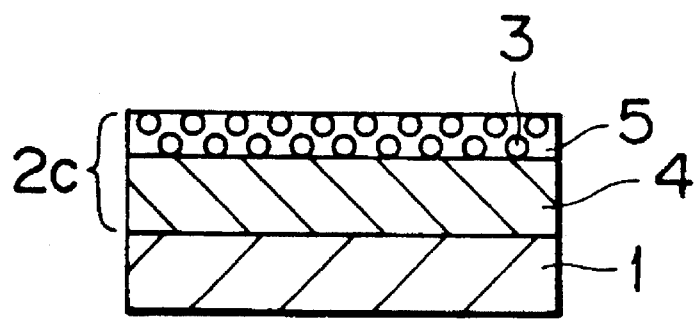
FIG. 4 is a schematic cross-sectional view of a fourth example of an electrophotographic photoconductor according to the present invention.

Referring to FIG. 4, there is shown still another embodiment of an electrophotographic photoconductor according to the present invention. In the figure, the overlaying order of the charge generation layer 5 and the charge transport layer 4 is reversed in view of the electrophotographic photoconductor as shown in FIG. 3. The mechanism of the generation and transportation of charge carriers is substantially the same as that of the photoconductor shown in FIG. 3.

Figure 5:
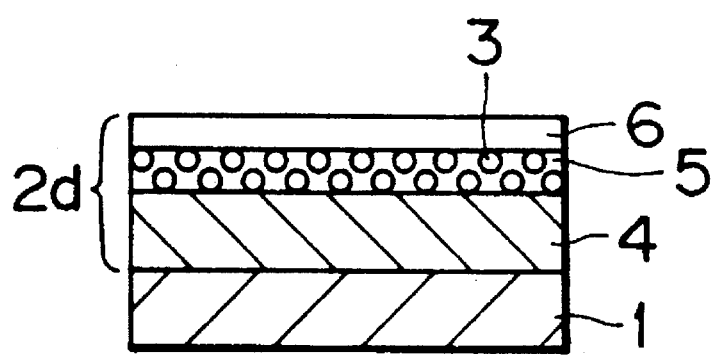
FIG. 5 is a schematic cross-sectional view of a fifth example of an electrophotographic photoconductor according to the present invention.

In the above photoconductor, a protective layer 6 may be formed on the charge generation layer 5 as shown in FIG. 5 for the improvement of the mechanical strength of the photoconductor.

When the electrophotographic photoconductor according to the present invention as shown in FIG. 1 is prepared, at least one diamine compound of the previously described formula (I) is dissolved In a binder resin solution, and a sensitizing dye is then added to the mixture, so that a photoconductive layer formation coating liquid is prepared. The thus prepared photoconductive layer formation coating liquid is coated on an electroconductive support 1 and dried, so that a photoconductive layer 2 is formed on the electroconductive support 1.

It is preferable that the thickness of the photoconductive layer 2 be in the range of 3 to 50 μm, more preferably in the range of 5 to 20 μm. It is preferable that the amount of the diamine compound contained in the photoconductive layer 2 be in the range or 30 to 70 wt. %, more preferably about 50 wt. %, of the total weight of the photoconductive layer 2.

It is preferable that the amount of the sensitizing dye contained in the photoconductive layer 2 be in the range of 0.1 to 5 wt. %, more preferably in the range of 0.5 to 3 wt. %, of the total weight of the photoconductive layer 2.

Specific examples of the sensitizing dye for use in the present invention are: triarylmethene dyes such as Brilliant Green, Victoria Blue B, Methyl Violet, Crystal Violet and Acid Violet 6B; xanthene dyes such as Rhodamine B, Rhodamine 6G, Rhodamine G Extra, Eosin S, Erythrosin, Rose Bengale and Fluoresceine; thiazine dyes such as Methylene Blue; cyanine dyes such as cyanin; and pyrylium dyes such as 2,6-diphenyl-4-(N,N-dimethylaminophenyl)thiapyrylium perchlorate and a benzopyrylium salt (described in Japanese Patent Publication 48-25658). These sensitizing dyes can be used alone or in combination.

The electrophotographic photoconductor shown in FIG. 2 can be prepared by dispersing finely-divided particles of the charge generating material 3 in a solution in which at least one diamine compound of formula (I) and the binder agent are dissolved, coating the above-prepared dispersion on the electroconductive support 1 and then drying the same to form the photoconductive layer 2a.

It is preferable that the thickness of the photoconductive layer 2a be in the range of 3 to 50 μm, more preferably in the range of 5 to 20 μm. It is preferable that the amount of the diamine compound contained in the photoconductive layer 2a be in the range or 10 to 95 wt. %, more preferably in the range of 30 to 90 wt. %, of the total weight of the photoconductive layer It is preferable that the amount of the charge generating material 3 contained in the photoconductive layer 2a be in the range of 0.1 to 50 wt. %, more preferably in the range of 1 to 20 wt. %, of the total weight of the photoconductive layer 2a.

Specific examples of the charge generating material 3 for use in the present invention are as follows: inorganic pigments such as selenium, selenium—tellurium, cadmium sulfide, cadmium sulfide—selenium and α-silicon (amorphous silicon); and organic pigments, such as C.I. Pigment Blue 25 (C.I. 21180), C.I. Pigment Red 41 (C.I. 21200), C.I. Acid Red 52 (C.I. 45100), and C.I. Basic Red 3 (C.I. 45210); an azo pigment having a carbazole skeleton (Japanese Laid-Open Patent Application 53-95033), an azo pigment having a distyryl benzene skeleton (Japanese Laid-Open Patent Application 53-133445), an azo pigment having a triphenylamine skeleton (Japanese Laid-Open Patent Application 53-132347), an azo pigment having a dibenzothiophene skeleton (Japanese Laid-Open Patent Application 54-21728), an azo pigment having an oxadiazole skeleton (Japanese Laid-Open Patent Application 54-12742), an azo pigment having a fluorenone skeleton (Japanese Laid-Open Patent Application 54-22834), an azo pigment having a bisstilbene skeleton (Japanese Laid-Open Patent Application 54-17733), an azo pigment having a distyryl oxadiazole skeleton (Japanese Laid-Open Patent Application 54-2129), and an azo pigment having a distyryl carbazole skeleton (Japanese Laid-Open Patent Application 54-14967); a phthalocyanine pigment such as C.I. Pigment Blue 16 (C.I. 74100); indigo pigments such as C.I. Vat Brown 5 (C.I. 73410) and C.I. Vat Dye (C.I. 73030); and perylene pigments such as Algol Scarlet B and Indanthrene Scarlet R (made by Bayer Co., Ltd.). These charge generating materials may be used alone or in combination.

The electrophotographic photoconductor shown in FIG. 3 can be prepared as follows:

The charge generating material 3 is vacuum-deposited on the electroconductive support 1 to form the charge generation layer 5 on the support 1. Alternatively, finely-divided particles of the charge generating material 3 are dispersed in an appropriate solvent, in which the binder agent may be dissolved when necessary, to prepare a dispersion, and the thus prepared dispersion is coated on the electroconductive support 1 and dried, so that the charge generation layer 5 is formed. When necessary, the charge generation layer 5 is subjected to surface treatment by buffing and adjustment of the thickness thereof. On the thus formed charge generation layer 5, a coating solution in which at least one diamine compound of formula (I) and the binder agent are dissolved is coated and dried, so that the charge transport layer 4 is formed. The same charge generating materials as employed in the previously-mentioned photoconductive layer 2a can be used in the charge generation layer 5.

In this case, the thickness of the charge generation layer 5 is 5 μm or less, more preferably 2 μm or less. It is preferable that the thickness of the charge transport layer 4 be in the range of 3 to 50 μm, more preferably in the range of 5 to 20 μm. When the charge generation layer 5 is formed by coating the dispersion of the finely-divided particles of the charge generating material 3, it is preferable that the amount of finely-divided particles of the charge generating material 3 contained in the charge generation layer 5 be in the range of 10 to 95 wt. %, more preferably in the range of about 50 to 90 wt. %, of the total weight of the charge generation layer 5. It is preferable that the amount of the diamine compound contained in the charge transport layer 4 be in the range of 10 to 95 wt. %, more preferably in the range of 30 to 90 wt. %, of the total weight of the charge transport layer 4.

The electrophotographic photoconductor shown in FIG. 4 can be prepared as follows:

A coating solution in which the diamine compound and the binder agent are dissolved is coated on the electroconductive support 1 and dried to form the charge transport layer 4. On the thus formed charge transport layer 4, a dispersion prepared by dispersing finely-divided particles of the charge generating material 3 in a solvent, in which the binder agent may be dissolved when necessary, is coated by spray coating and dried to form the charge generation layer 5 on the charge transport layer 4. The amount ratio of the components contained in the charge generation layer and charge transport layer is the same as previously described in FIG. 3.

The electrophotographic photoconductor shown in FIG. 5 can be prepared by forming a protective layer 6 on the charge generation layer 5 as obtained in FIG. 4 by spray-coating of an appropriate resin solution. As a resin for use in the protective layer 6, any of binder agents to be described later can be used.

Specific examples of the material for the electroconductive support 1 include a metallic plate or foil made of aluminum, a plastic film on which a metal such as aluminum is deposited, and a sheet of paper which has been treated so as to be electroconductive.

Specific examples of the binder agent used in the preparation of the photoconductor including the protective layer therefor are condensation resins such as polyamide, polyurethane, polyester, epoxy resin, polyketone and polycarbonate; and vinyl copolymers such as polyvinylketone, polystyrene, poly-N-vinylcarbazole and polyacrylamide. All the resins can be employed so longs they have insulating properties and adhesiveness.

Some plasticizers may be added go the above-mentioned binder agent, when necessary. Examples of the plasticizer for use in the present invention are halogenated paraffin, polybiphenyl chloride, dimethylnaphthalene and dibutyl phthalate.

Furthermore, in the electrophotographic photoconductor according to the present invention, an adhesive layer or a barrier layer may be interposed between the electroconductive support and the photoconductive layer when necessary. Examples of the material for use in the adhesive layer or barrier layer are polyamide, nitrocellulose and aluminum oxide. It is preferable that the thickness of the adhesive layer or barrier layer be 1 μm or less.

When copying is performed by use of the photoconductor according to the present invention, the surface of the photoconductor is uniformly charged to a predetermined polarity in the dark. The uniformly charged photoconductor is exposed to a light image so that a latent electrostatic image is formed on the surface of the photoconductor. The thus formed latent electrostatic image is developed to a visible image by a developer, and the developed image can be transferred to a sheet of paper when necessary. The photoconductor according to the present invention has excellent photosensitivity and flexibility.

Other features of this invention will become apparent in the course of the following description of exemplary embodiments, which are given for illustration of the invention and are not intended to be limiting thereof.

Furthermore, the reference number of each diamine compound employed in the following examples is indicated by the combination of the reference numbers of the starting materials for the elm thesis of the diamine compound, namely, by the combination of the reference numbers of the hydroxy compound and the bis(chloroformate) compound for the synthesis of the diamine compound.

SYNTHESIS EXAMPLE

Synthesis of Diamine Compound No. 1-11

3.14 g (12.0 mmol) of 4-hydroxytriphenylamine (Hydroxy Compound No. 1) and 1.86 g (14.4 mmol) of quinoline were dissolved in 20 ml of dried dichloromethane. To this solution, a solution of 2.12 g (6.00 mmol) of 4,4'-isopropylidenediphenol-bis(chloroformate) (Bis (chloroformate) Compound No. 11) in 20 ml of dried dichloromethane was added dropwise in a stream of nitrogen at room temperature over a period of 15 minutes.

The reaction mixture was stirred at 40° C. for 4 hours. Then, the reaction mixture was washed with water three times, and then with a saturated aqueous solution of sodium chloride once, using a separating funnel. Thereafter, the reaction mixture was dried over magnesium sulfate and concentrated under reduced pressure to yield a green oily material. The resulting product was chromatographed on a silica gel column by using a mixed solvent of toluene and n-hexane with a volume ratio of 3:1 as an eluting solution. Then, the compound thus obtained was recrystallized from a mixed solvent of toluene and n-hexane, so that a diamine compound No. 1-11 with the following formula was obtained in the form of colorless plates. The yield was 2.52 g (52.3%).

The melting point of the above obtained diamine compound No. 1-11 was 204.0° to 205.5° C.

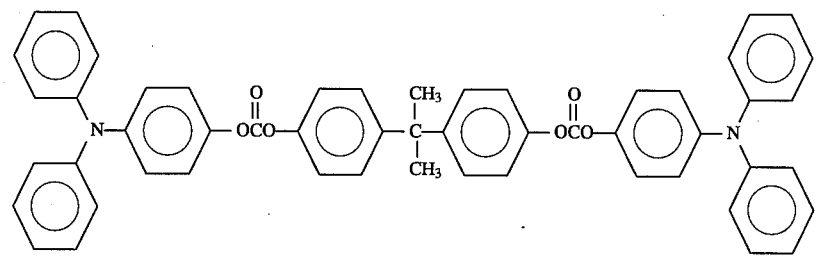

The results of the elemental analysis of the thus obtained compound were as follows:

|  | % C | % H | % N |
|---|---|---|---|
| Found | 79.56 | 4.96 | 3.25 |
| Calculated | 79.28 | 5.27 | 3.49 |

The above calculation was based on the formula for $C_{53}H_{42}N_2O_6$.

EXAMPLE 1

76 parts by weight of Diane Blue (C.I. Pigment Blue 25, CI21180) serving as a charge generating material, 1260 parts by weight of a 2% tetrahydrofuran solution of a polyester resin (Trademark "Vylon 200" made by Company, Ltd.) and 3700 parts by weight of tetrahydrofuran were dispersed and ground in a ball mill. The thus prepared dispersion was coated on an aluminum surface of an aluminum-deposited polyester film by a doctor blade, and dried at room temperature, so that a charge generation layer having a thickness of about 1 μm was formed on the aluminum-deposited polyester film.

2 parts by weight of the diamine compound No. 3-11, 2 parts by weight of polycarbonate resin (Trademark "Panlite K-1300" made by Teijin Limited.) and 16 parts by weight of tetrahydrofuran were mixed to form a coating solution for the formation of a charge transport layer.

This coating solution was coated on the above formed charge generation layer by a doctor blade and then dried at 80° C. for 2 minutes and then at 120° C. for 5 minutes, so that a charge transport layer having a thickness of about 20 μm was formed on the charge generation layer.

Thus, a two-layered electrophotographic photoconductor No. 1 according to the present invention was prepared.

EXAMPLES 2 to 21

The procedure for preparation of the two-layered electrophotographic photoconductor No. 1 in Example 1 was repeated except that Diane Blue serving as the charge generating material and the diamine compound No. 3-11 serving as the charge transporting material employed in Example 1 were respectively replaced by the charge generating materials and charge transporting materials listed in the following Table 4, whereby two-layered electrophotographic photoconductors No. 2 to No. 21 of the present invention were prepared.

TABLE 4

| Photoconductor No. | Charge Generating Material | Charge Transporting Material (Diamine Compound No.) |
|---|---|---|
| 1 | | 3-11 |
| 2 | | 3-11 |
| 3 | (hereinafter referred to as P-1.) | 3-11 |

TABLE 4-continued
| Photoconductor No. | Charge Generating Material | Charge Transporting Material (Diamine Compound No.) |
|---|---|---|
| 4 | 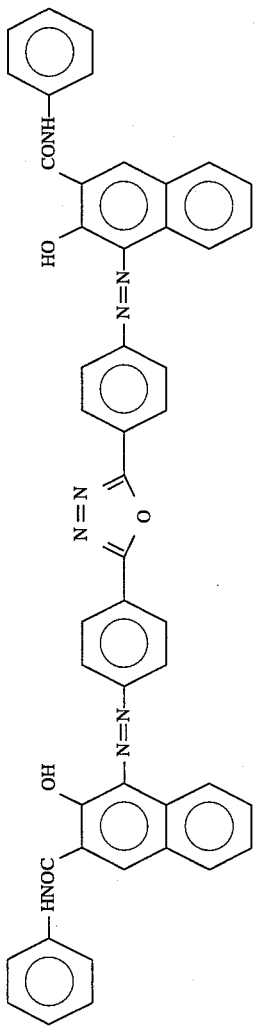 | 3-11 |
| 5 | 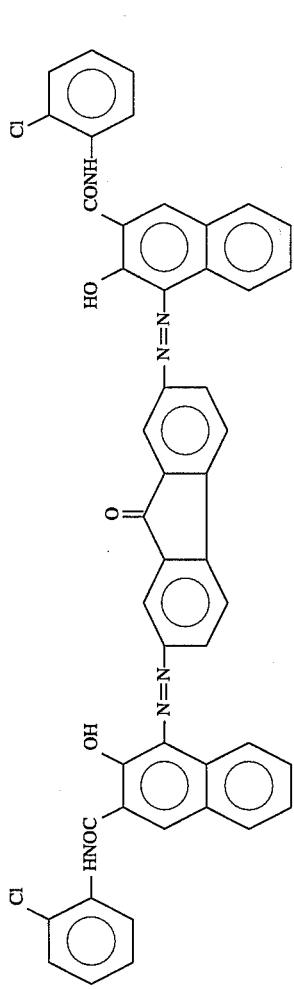 | 3-11 |
| 6 | 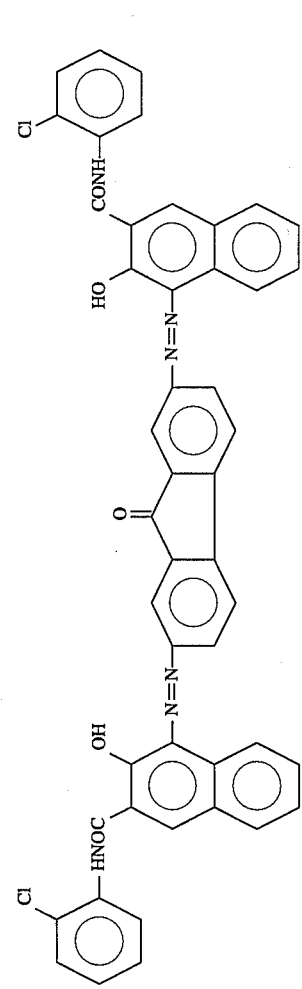 (hereinafter referred to as P-2.) 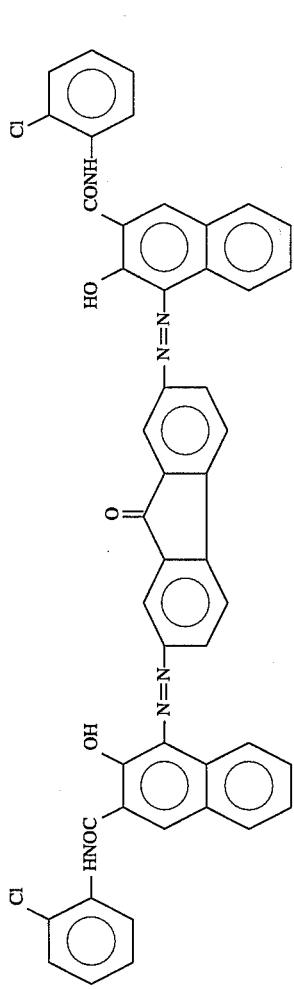 (hereinafter referred to as P-3.) | 3-11 |

TABLE 4-continued

| Photoconductor No. | Charge Generating Material | Charge Transporting Material (Diamine Compound No.) |
|---|---|---|
| 7 | β-type Copper Phthalocyanine | 3-11 |
| 8 | (structure with OCH₃ substituents, azo-linked bis-naphthol bisphenylamide) | 2-11 |
| 9 | (structure with Cl substituents, azo-linked bis-naphthol bisphenylamide) | 2-11 |
| 10 | P-1 | 2-11 |
| 11 | P-2 | 2-11 |
| 12 | P-3 | 2-11 |
| 13 | P-1 | 1-11 |
| 14 | P-2 | 1-11 |
| 15 | P-3 | 1-11 |
| 16 | P-1 | 31-21 |
| 17 | P-2 | 31-21 |
| 18 | P-3 | 31-21 |
| 19 | P-1 | 58-7 |
| 20 | P-2 | 58-7 |
| 21 | P-3 | 58-7 |

EXAMPLE 22

Selenium was vacuum-deposited on an aluminum plate having a thickness of about 300 μm, so that a selenium charge generation layer having a thickness of about 1 μm was formed on the aluminum plate.

2 parts by weight of the diamine compound No. 3-11, 3 parts by weight of polyester resin (Trademark "Polyester Adhesive 49000" made by Du Pont de Nemours, E. I. & Co.) and 45 parts by weight of tetrahydrofuran were mixed to form a coating liquid for the formation of a charge transport layer. This coating liquid was coated on the above formed charge generation layer by a doctor blade, dried at room temperature and then under reduced pressure, so that a charge transport layer with a thickness of about 10 μm was formed on the charge generation layer.

Thus, a two-layered electrophotographic photoconductor No. 22 according to the present invention was prepared.

EXAMPLE 23

The procedure for preparation of the two-layered electrophotographic photoconductor No. 22 in Example 22 was repeated except that a charge generation layer with a thickness of about 0.6 μm was formed on the same aluminum plate as employed in Example 22 by deposition of a perylene pigment of formula (A) instead of selenium, so that a two-layered electrophotographic photoconductor No. 23 according to the present invention was prepared.

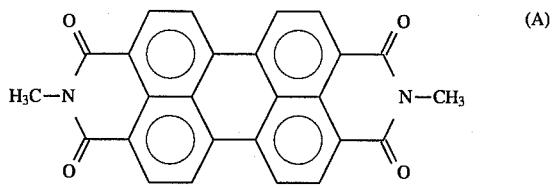

(A)

EXAMPLE 24

A mixture of one part by weight of the same Diane Blue as employed in Example 1 and 158 parts by weight of tetrahydrofuran was dispersed and ground in a ball mill to form a dispersion. To the thus formed dispersion, 12 parts by weight of the diamine compound No. 3-11, and 18 parts by weight of polyester resin (Trademark "Polyester Adhesive 49000" made by Du Pont de Nemours, E. I. & Co.) were added to form a coating liquid for the formation of a photoconductive layer.

This coating liquid was coated on an aluminum surface of an aluminum-deposited polyester film by a doctor blade, and dried at 100° C. for 30 minutes, so that a photoconductive layer having a thickness of about 16 μm was formed on the electroconductive support.

Thus, an electrophotographic photoconductor No. 24 according to the present invention was prepared.

EXAMPLE 25

2 parts by weight of the diamine compound No. 3-11, 2 parts by weight of polycarbonate resin (Trademark "Panlite K-1300" made by Teijin Limited.) and 16 parts by weight of tetrahydro-furan were mixed to prepare a coating liquid for the formation of a charge transport layer.

This coating liquid was coated on an aluminum surface of an aluminum-deposited polyester film by a doctor blade and dried at 80° C. for 2 minutes, and then at 120° C. for 5 minutes in the same manner as in Example 1, whereby a charge transport layer with a thickness of about 20 μm was formed on the aluminum-deposited polyester film.

A mixture of 13.5 parts by weight of the bisazo pigment (P-2) shown in Table 4, 5.4 parts by weight of polyvinyl butyral (Trademark "XYHL" made by Union Carbide Japan K.K.), 680 parts by weight of tetrahydrofuran and 1020 parts by weight of ethyl cellosolve was dispersed and ground in a ball mill. To this dispersion, 1700 parts by weight of ethyl cellosolve were further added to prepare a coating liquid for the formation of a charge generation layer.

This coating liquid was coated on the above formed charge transport layer by spray coating and dried at 100° C. for 10 minutes, so that a charge generation layer having a thickness of about 0.2 μm was formed on the charge transport layer.

A methanol—n-butanol solution of a polyemide resin (Trademark "CM-8000" made by Toray Silicone Co., Ltd.) was coated on the above formed charge generation layer by spray coating and dried at 120° C. for 30 minutes, so that a protective layer with a thickness of about 0.5 μm was formed on the charge generation layer.

Thus, an electrophotographic photoconductor No. 25 according to the present invention was prepared.

Each of the electrophotographic photoconductors No. 1 through No. 25 according to the present invention prepared in Examples 1 to 25 was charged negatively or positively in the dark under application of −6 kV or +6 kV of corona charge for 20 seconds, using a commercially available electrostatic copying sheet testing apparatus ("Paper Analyzer Model SP-428" made by Kawaguchi Electro works Co., Ltd.). Then, each electrophotographic photoconductor was allowed to stand in the dark for 20 seconds without applying any charge thereto, and the surface potential Vpo (V) of the photoconductor was measured. Each photoconductor was then illuminated by a tungsten lamp in such a manner that the illuminance on the illuminated surface of the photoconductor was 4.5 lux, and the exposure $E_{1/2}$ (lux.sec) required to reduce the initial surface potential Vpo (V) to ½ the initial surface potential Vpo (V) was measured. The results are shown in Table 5.

TABLE 5

| Photoconductor No. | Vpo (V) | $E_{1/2}$ (lux · sec) |
|---|---|---|
| 1 | −1325 | 1.40 |
| 2 | −1411 | 1.52 |
| 3 | −1322 | 1.50 |
| 4 | −1413 | 1.59 |
| 5 | −1456 | 1.55 |
| 6 | −1328 | 1.24 |
| 7 | −1051 | 1.13 |
| 8 | −1256 | 1.52 |
| 9 | −1321 | 1.46 |
| 10 | −1511 | 1.88 |
| 11 | −1542 | 1.97 |
| 12 | −1313 | 1.31 |
| 13 | −1625 | 2.90 |
| 14 | −1730 | 2.97 |
| 15 | −1388 | 1.36 |
| 16 | −1356 | 1.13 |
| 17 | −1405 | 1.09 |
| 18 | −926 | 0.56 |
| 19 | −1421 | 1.51 |
| 20 | −1356 | 1.42 |
| 21 | −1311 | 1.10 |

TABLE 5-continued

| Photoconductor No. | Vpo (V) | $E_{1/2}$ (lux · sec) |
|---|---|---|
| 22 | −1567 | 1.88 |
| 23 | −826 | 1.36 |
| 24 | +1354 | 1.48 |
| 25 | +1254 | 1.21 |

Each of the above prepared electrophotographic photoconductors of the present invention was uniformly charged and then exposed to a light image through an original to be copied by use of a commercially available electrophotographic copying machine, whereby a latent electrostatic image corresponding to the light image was formed thereon.

The thus formed latent electrostatic image was developed with a dry type developer to form a toner image. The thus formed toner image was transferred electrostatically to a plain paper and fixed thereto, whereby a clear transferred image was obtained by each of the electrophotographic photoconductors.

When a liquid developer was employed instead of the dry type developer, a clear transferred image was also obtained in the same manner as in the case where the dry type developer was used.

The electrophotographic photoconductor of the present invention, which employs the diamine compound of formula (I) as an effective photoconductive material, has not only excellent photosensitive characteristics, but also high resistance to heat and mechanical shocks, and the production cost of the photoconductor is inexpensive.

Japanese Patent Application 5-20006 filed on Jul. 19, 1993 and Japanese Patent Application 5-242070 filed Sep. 2, 1993 are hereby incorporated by reference.

What is claimed is:

1. An electrophotographic photoconductor comprising:
   an electroconductive support, and
   a photoconductive layer formed thereon which comprises as a photoconductive material at least one diamine compound having carbonate groups of formula (I):

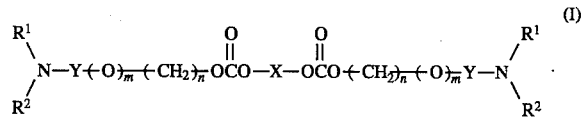

(I)

wherein $R^1$ and $R^2$ each is a hydrogen atom, an alkyl group which may have a substituent, an aryl group which may have a substituent; $R^1$ and $R^2$ may fore a ring in combination of N bonded thereto; Y is an arylene group which may have a substituent, $$-Ar^1\!+\!C\!=\!C\!\frac{}{l}Ar^2\!-, \text{ or } -Ar^1\!+\!CH\!-\!CH\!\frac{}{l}Ar^2\!-,$$
$$\phantom{-Ar^1+}R^3\ R^4 \phantom{\text{ or } -Ar^1+}R^3\ R^4$$

in which $Ar^1$ and $Ar^2$ each is en arylene group which may have a substituent, $R^3$ and $R^4$ each is e hydrogen atom, an alkyl group which may have a substituent or an aryl group which may have a substituent, and l is an integer of 1 or 2; and $R^1$ and Y may together form a ring, X is an alkylene group which may have a substituent, a dialkylene ether group, or an arylene group which may have a substituent, $$-Ar^3\text{-Z-}Ar^4-,$$

in which $Ar^3$ and $Ar^4$ each is an arylene group which may have a substituent; Z is an alkylene group which may have a substituent, a dialkylene ether group or a cycloalkylidene group which may have a substituent, an oxygen atom, q sulfur atom, a vinylene group, m is an integer of 0 or 1; and n is an integer of 0 to 6.

2. The electrophotographic photoconductor as claimed in claim 1, wherein said photoconductive layer further comprises a binder agent which constitutes a charge transporting medium in combination with said diamine compound; and a charge generating material dispersed within said charge transporting medium.

3. The electrophotographic photoconductor as claimed in claim 1, wherein said photoconductive layer comprises a charge generation layer containing a charge generating material, and a charge transport layer containing said diamine compound as a charge transporting material.

4. The electrophotographic photoconductor as claimed in claim 1, wherein the amount of said diamine compound is in the range of 30 wt. % to 70 wt. % of the entire weight of said photoconductive layer.

5. The electrophotographic photoconductor as claimed in claim 2, wherein the amount of said diamine compound is in the range of 10 wt. % to 95 wt. % of the entire weight of said photoconductive layer, and the amount of said charge generating material is in the range of 0.1 wt. % to 50 wt. % of the entire weight of said photoconductive layer.

6. The electrophotographic photoconductor as claimed in claim 3, wherein the amount of said charge generating material is in the range of 10 wt. % to 95 wt. % of the entire weight of said charge generation layer, and the amount of said diamine compound is in the range of 10 wt. % to 95 wt. % of the entire weight of said charge transport layer.

* * * * *

UNITED STATES PATENT AND TRADEMARK OFFICE
CERTIFICATE OF CORRECTION

PATENT NO. : 5,480,753
DATED : JANUARY 2, 1996
INVENTOR(S) : TOMOYUKI SHIMADA ET AL

It is certified that error appears in the above-identified patent and that said Letters Patent is hereby corrected as shown below:

| Col. | Line | |
|---|---|---|
| 1, | 4, | "end" should read --and--; |
| | 19, | "end" should read --and--. |
| 2, | 20, | "and considered" should read --and are considered--. |
| 3, | 7, | "easily be manufactured" should read --easily manufactured--; |
| | 50, | "Of" should read --of--. |
| 4, | 45, | "specific" should read --Specific--. |
| 6, | 25, | "$Ar^5$" should read --$Ar^6$--. |
| 27, | 32, | "or" should read --of--. |
| 29, | 30, | "longs" should read --long as--; |
| | 32, | "go" should read --to--. |
| 30, | 10, | "elm-thesis" should read --synthesis--. |
| 31, | 6, | "by Company" should read --by Toyobo Company--. |
| 39, | 66, | "tetrahydro-furan" should read --tetrahydrofuran--. |

UNITED STATES PATENT AND TRADEMARK OFFICE
CERTIFICATE OF CORRECTION

PATENT NO.    : 5,480,753
DATED         : JANUARY 2, 1996
INVENTOR(S)   : TOMOYUKI SHIMADA ET AL

It is certified that error appears in the above-identified patent and that said Letters Patent is hereby corrected as shown below:

Col.   Line 41,    50,  "fore" should read --form--.
42,     6,  "en" should read --an--;
        7,  "e" should read --a--;
       21,  "q" should read --a--.

Signed and Sealed this

Fifth Day of November, 1996

Attest:

BRUCE LEHMAN

Attesting Officer    Commissioner of Patents and Trademarks